US00PP35226P3

(12) United States Plant Patent
Kim et al.

(10) Patent No.: US PP35,226 P3
(45) Date of Patent: Jun. 20, 2023

(54) ***CITRUS* TREE NAMED 'JEDAE'**

(50) Latin Name: *Citrus unshiu*
Varietal Denomination: Jedae

(71) Applicant: JEJU NATIONAL UNIVERSITY INDUSTRY-ACADEMIC COOPERATION FOUNDATION, Jeju-si (KR)

(72) Inventors: In-Jung Kim, Jeju-si (KR); Ji-Man Heo, Jeju-si (KR)

(73) Assignee: JEJU NATIONAL UNIVERSITY INDUSTRY-ACADEMIC COOPERATION FOUNDATION, Jeju-si (KR)

( * ) Notice: Subject to any disclaimer, the term of this patent is extended or adjusted under 35 U.S.C. 154(b) by 0 days.

(21) Appl. No.: 17/300,745

(22) Filed: Oct. 21, 2021

(65) Prior Publication Data

US 2022/0053677 P1 Feb. 17, 2022

Related U.S. Application Data

(63) Continuation of application No. 15/740,806, filed as application No. PCT/KR2016/006967 on Jun. 29, 2016, now abandoned.

(30) Foreign Application Priority Data

Jun. 29, 2015 (KR) ..... 10-2015-0092516
Jun. 29, 2016 (KR) ..... 10-2016-0081748

(51) Int. Cl.
*A01H 5/08* (2018.01)
*A01H 6/78* (2018.01)

(52) U.S. Cl.
USPC ..... Plt./201
CPC ..... *A01H 5/08* (2013.01)

(58) Field of Classification Search
USPC ..... Plt./156, 201
See application file for complete search history.

(56) References Cited

U.S. PATENT DOCUMENTS

| | | | | |
|---|---|---|---|---|
| PP8,378 | P | 9/1993 | Vardi et al. | |
| PP23,724 | P2 | 7/2013 | McCollum et al. | |
| 8,592,661 | B1 | 11/2013 | Willard et al. | |
| 2007/0056064 | P1 | 3/2007 | Roose et al. | |
| 2014/0090121 | P1 * | 3/2014 | Combrink | A01H 5/08 Plt./201 |

FOREIGN PATENT DOCUMENTS

| | | |
|---|---|---|
| KR | 10-0532072 B1 | 11/2005 |
| KR | 10-0759132 B1 | 9/2007 |

OTHER PUBLICATIONS

Chang-Ho. 2002. Plants 2022, 11: 1337. (Year: 2022).*
International Search Report for PCT/KR2016/006967 dated Jan. 13, 2017 from Korean Intellectual Property Office.
Kim, In Jung et al., "Induction and Selection of Citrus Mutant by Gamma-Irradiation", Journal of Radiation Industry, 2010, vol. 4, No. 3, pp. 215-219.

* cited by examiner

*Primary Examiner* — Karen M Redden
(74) *Attorney, Agent, or Firm* — Revolution IP, PLLC

(57) ABSTRACT

A new and distinct variety of '*C. unshiu* Marc. cv. Miyagawa-wase', plant named 'Jedae', this new variety *Citrus* plant is an early-maturing satsuma mandarin reproduced and propagated asexually, and characterized by i) rough peel, ii) vertical corrugation from fruit stalk which results in uneven outer appearance of fruit, and iii) higher flavonoid content in the fruit, compared to 'Miyagawa-wase'.

17 Drawing Sheets

The Latin name of the genus and species is: *Citrus unshiu.* The variety denomination is: 'Jedae'.

BACKGROUND OF THE INVENTION

The present invention relates to a new and distinct variety of a mandarin tree named 'Jedae', which originated from '*C. unshiu* Marc. cv. Miyagawa-wase' of early-maturing satsuma mandarin which is the most cultivated varieties in Jeju Island, Korea. 'Jedae' was obtained from 'Miyagawa-wase' by a radiation-induced mutation. The new mandarin variety is an early-maturing satsuma mandarin characterized by fruit shape and flavonoid components altered by artificial mutation breeding involving the gamma irradiation compared to 'Miyagawa-wase'.

BRIEF SUMMARY OF THE INVENTION

The present invention related to a new and distinct variety of 'Miyagawa-wase', plant named 'Jedae'. 'Miyagawa-wase' is the closest comparison to 'Jedae'. The new variety *Citrus* plant is an early-maturing satsuma mandarin reproduced and propagated asexually by grafting in Seogwipo-si, Jeju Special Self-Governing Province, Korea from 2006 first and then further reproduced during 2006 to 2013, and characterized by i) rough peel, ii) vertical corrugation from fruit stalk which results in uneven outer appearance of fruit, and iii) higher flavonoid content in the fruit, compared to 'Miyagawa-wase'.

In detail, the fruits of 'Jedae' were slightly larger than those of 'Miyagawa-wase'. In addition, the fruits of 'Jedae' had the peels that were less smooth and more rugged on outer surface in terms of fruit shape, compared to fruits of 'Miyagawa-wase'. The fruits of 'Jedae' had groove of radial shape from the fruit stalk and were found to have vertical corrugation in overall way when they were viewed from the side. Thus, the fruits of 'Jedae' were considered to have excellent fruit shape and have the potential to be developed into decorative *Citrus* fruits. The flavonoid, a functional substance contained in *Citrus* fruits, is typified by components such as hesperidin (HD) and narirutin (NRT). Such the flavonoid content was contained more in the fruit of 'Jedae' compared to 'Miyagawa-wase' cultivated under the same conditions.

DETAILED BOTANICAL DESCRIPTION

The following is a detailed description of the new mandarin based on observations taken of a 7 year-old specimen grown in Donghong-dong, Seogwipo-si, Jeju Special Self-Governing Province, Korea. The color descriptions are all based on The Royal Horticultural Society Colour Chart, 2007, Fifth edition.

Figure 1:
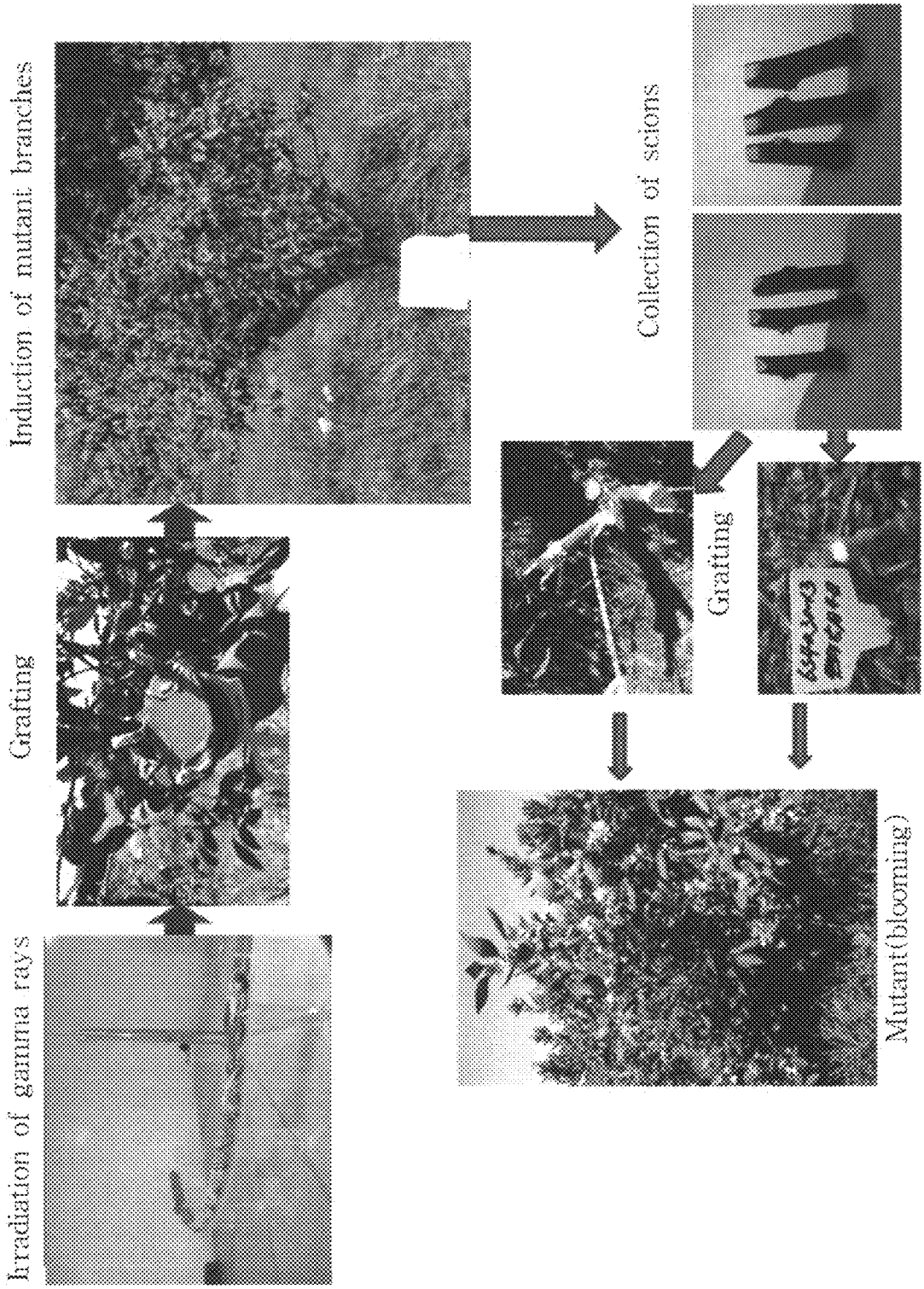
FIG. 1 shows the obtaining process of 'Jedae' by a radiation-induced mutation (the age of photographed 'Jedae': 7 years).
Figure 2:
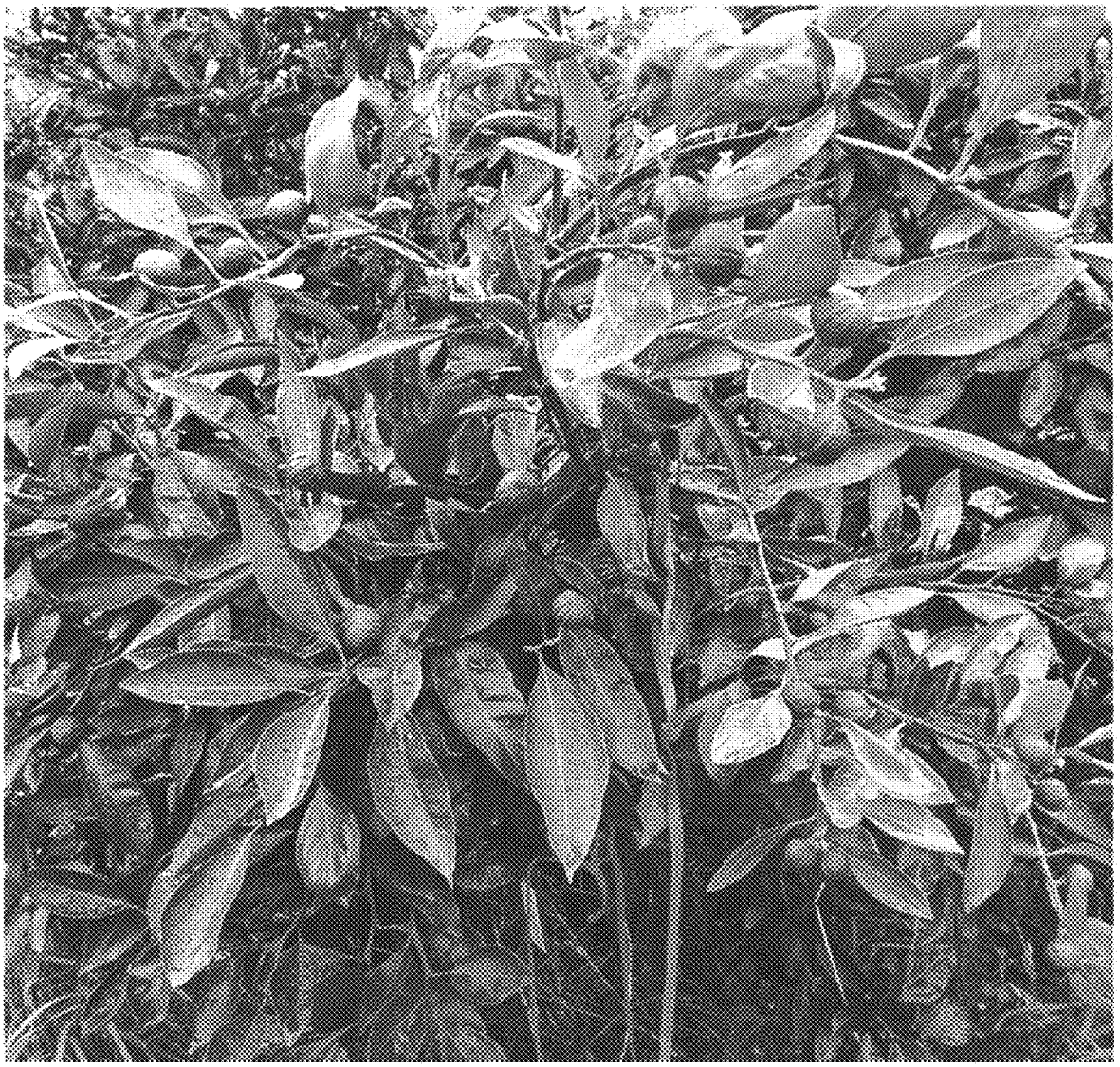
FIG. 2 shows a 'Jedae' *Citrus* tree bearing the fruit (photograph taken on Jul. 2, 2013 and cultivated in Donghong-dong, Seogwipo-si, Jeju Special Self-Governing Province, Korea, the age of photographed 'Jedae': 7 years).
Figure 3:
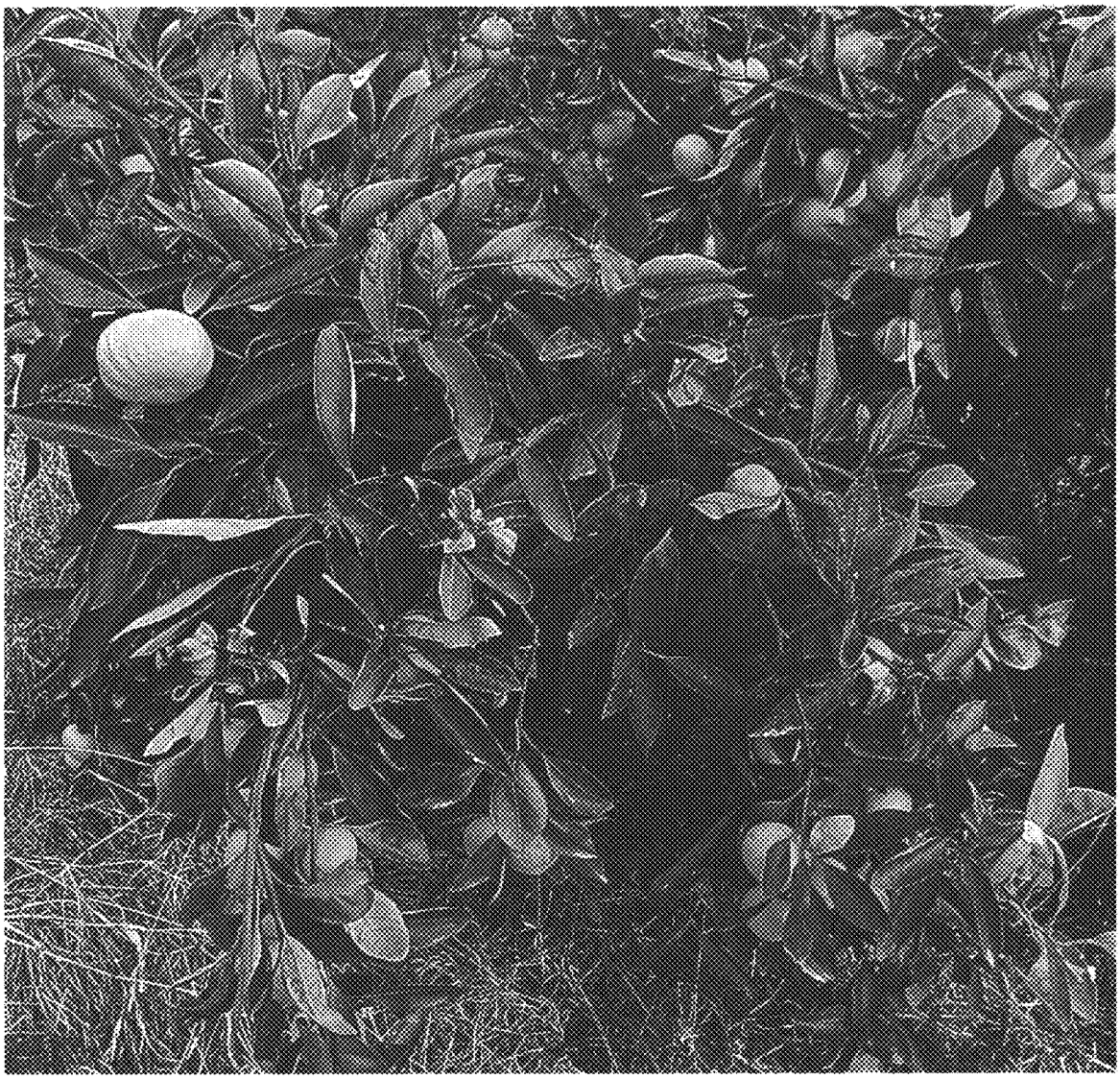
FIG. 3 shows a 'Jedae' *Citrus* tree bearing the fruit (photograph taken on Nov. 20, 2013 and cultivated in Donghong-dong, Seogwipo-si, Jeju Special Self-Governing Province, Korea, the age of photographed 'Jedae': 7 years).
Figure 4:
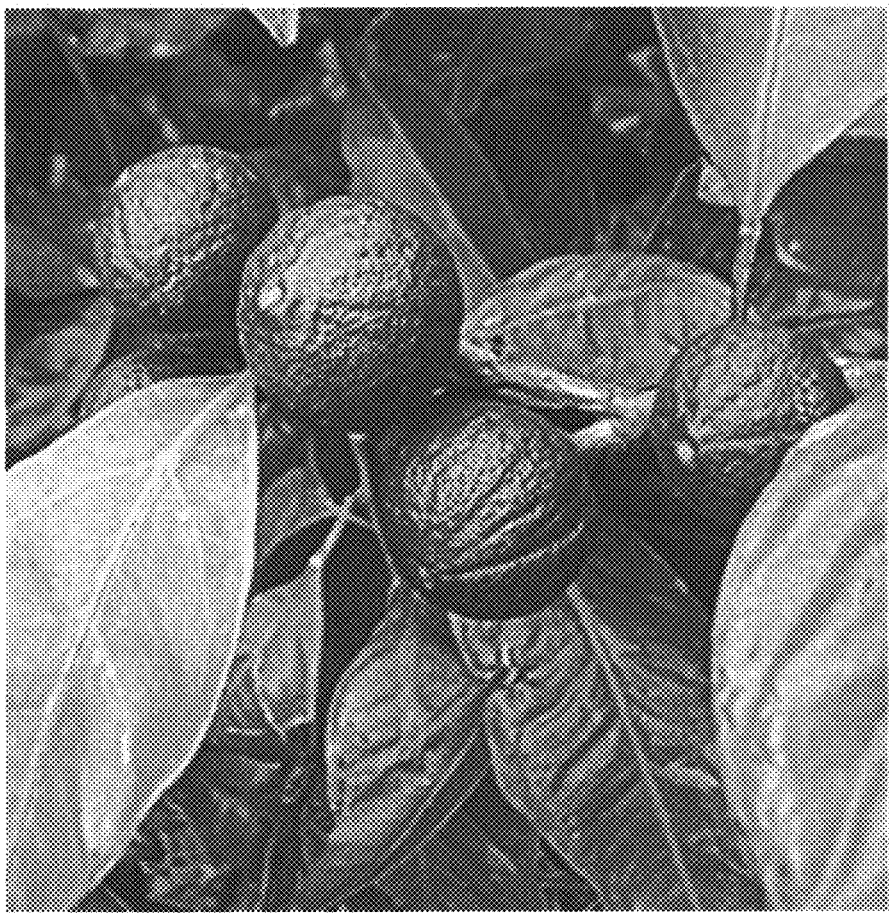
FIG. 4 shows the fruit of mutant *Citrus* 'Jedae' (photograph taken in early July 2013 and the age of photographed 'Jedae': 7 years).
Figure 5:
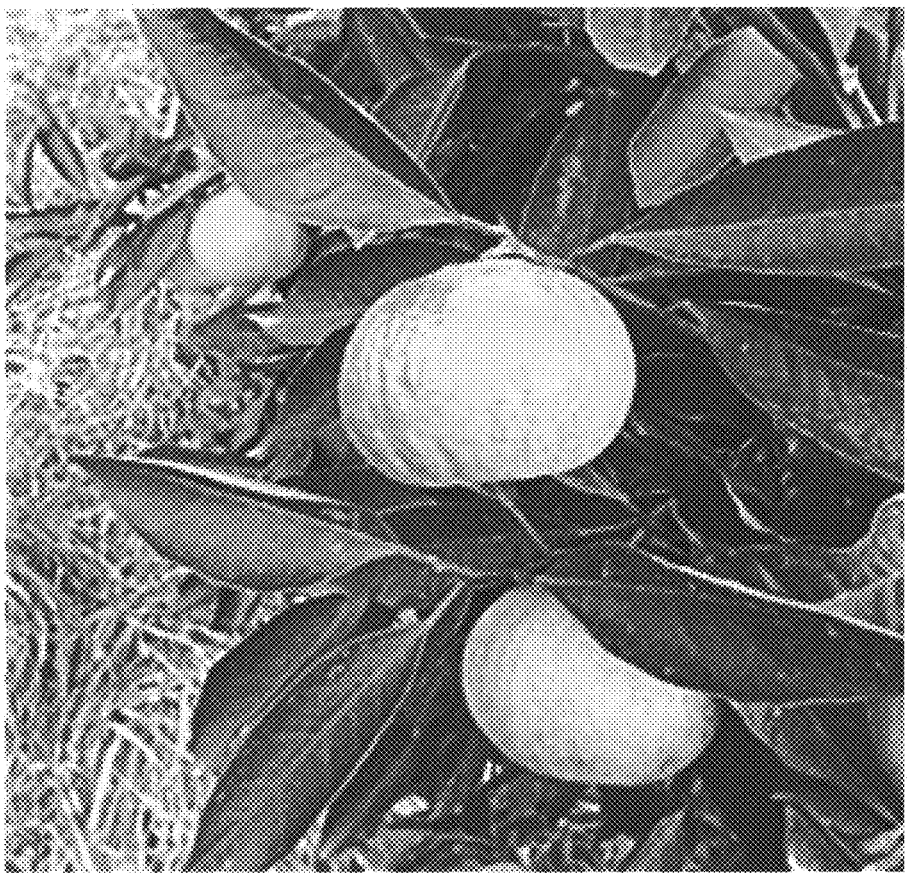
FIG. 5 shows the fruit of mutant *Citrus* 'Jedae' (photograph taken in early November 2013 and the age of photographed 'Jedae': 7 years).
Figure 6:
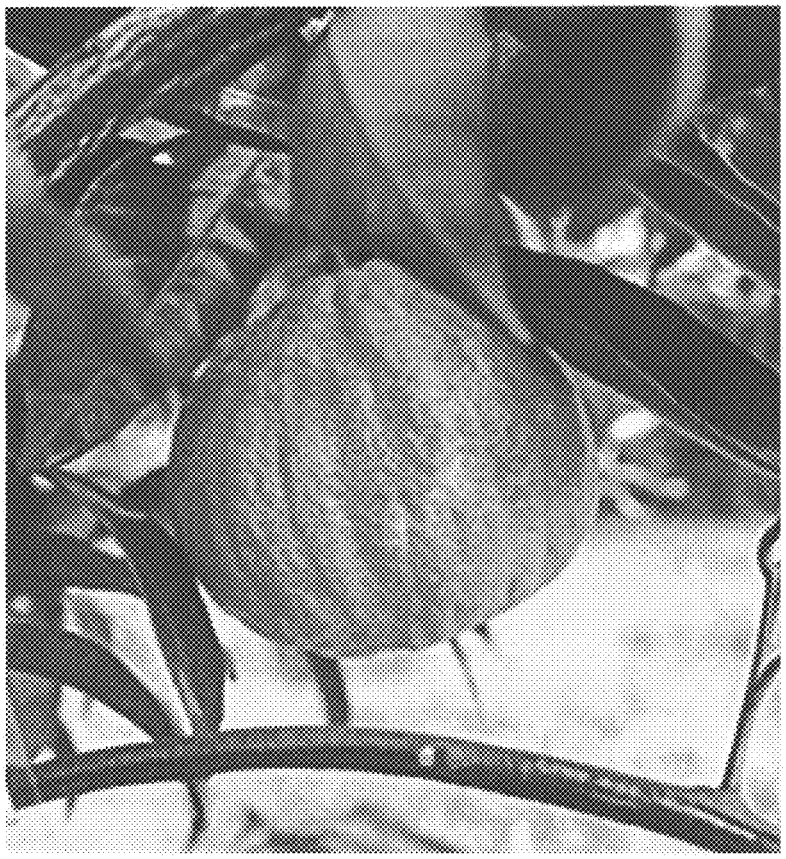
FIG. 6 shows the fruit of mutant *Citrus* 'Jedae' (photograph taken in early December 2013 and the age of photographed 'Jedae': 7 years).
Figure 7:
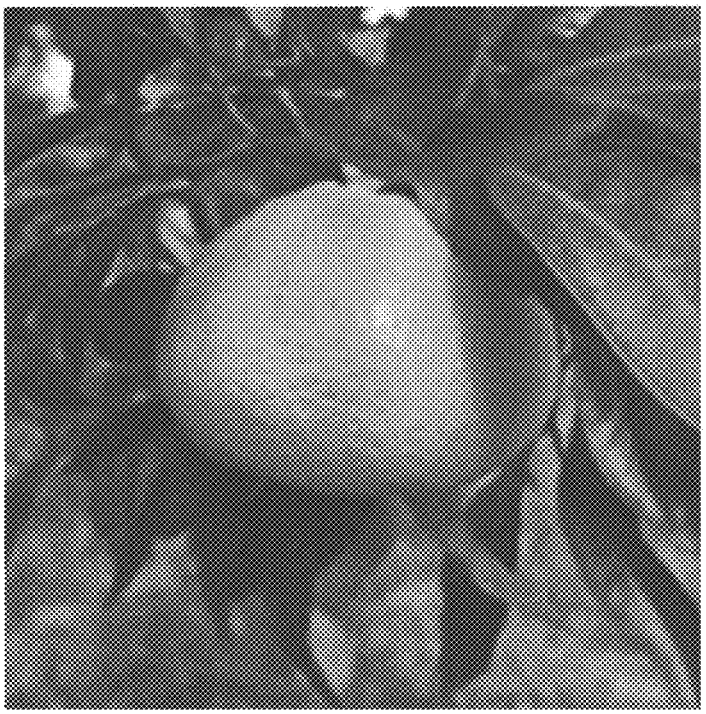
FIG. 7 shows the fruit of 'Miyagawa-wase' cultivated under the conditions same as 'Jedae' (photograph taken in early December 2013 and the age of photographed 'Jedae': 7 years).

As described above, 'Jedae' was obtained from 'Miyagawa-wase' by radiation-induced mutation, as shown in FIG. 1. The analyses on characteristics of 'Jedae' are described as follows.

1) Tree Characteristics

The following shows botanical characteristics of 'Jedae' (Table 1).

TABLE 1

| Vitality of Tree | Blooming Period | Coloring of Peel | Period of Harvesting |
|---|---|---|---|
| Moderate | From May 10 to 20 | Late November | From late November to mid-December |

The following shows flower characteristics (Table 2).

TABLE 2

| | |
|---|---|
| Length of calyx (mm) | 4.21 ± 0.51 |
| Width of calyx (mm) | 3.41 ± 0.22 |
| Length of petal (mm) | 18.91 ± 1.86 |
| Width of petal (mm) | 6.20-0.92 |
| Ratio of length of petal/width of petal | 3.10-0.47 |
| Length of stamen (mm) | 10.64 ± 1.09 |
| Number of stamen (number) | 20.11 ± 3.60 |
| Anther color | Light yellow (RHS, Yellow orange 15C) |
| Length of style (mm) | 11.10 ± 0.78 |
| Diameter of style (mm) | 1.73 ± 0.17 |
| Pollen germination rate (%) | 12.06 |

(The color descriptions are all based on The Royal Horticultural Society Colour Chart, 2007, Fifth edition)

The following shows leave characteristics (Table 3).

TABLE 3

| | |
|---|---|
| Leaf blade length (mm) | 87.40 ± 11.95 |
| Leaf blade width (mm) | 38.40 ± 5.08 |
| Leaf blade length/width ratio | 2.53 ± 0.26 |
| Leaf blade cross section shape | 1.46 ± 0.74 (straight or slightly concave: 1/medium: 2/severe: 3) |
| Leaf blade twisting | 1.07 ± 0.26 (no or slight: 1/medium: 2/severe: 3) |
| Leaf blade surface upheaval | 1.18 ± 0.48 (no or slight: 1/medium: 2/severe: 3) |
| Leaf blade green degree | 3.21 ± 0.63 (light: 3/medium: 5/dark: 7) |

TABLE 3-continued

| | |
|---|---|
| Leaf blade wavy edges | 1.29 ± 0.60 (no or slight: 1/medium: 2/severe: 3) |
| Leaf blade incisions of margin | 2.00 ± 0.00 (no: 1/crenate: 2/serrated: 3) |
| Leaf blade shape of apex | 1.61 ± 0.50 (pointed: 1/sharp: 2/blunt: 3/round: 3) |
| Leaf blade apical groove | 4.43 ± 4.03 (absent: 1/present: 9) |
| Petiole length (mm) | 18.96 ± 3.26 |
| Petiole presence or absence of wing | 1.57 ± 2.10 (absent: 1/present: 9) |
| Petiole width of wing (mm) | 4.06 ± 0.08 |

The leaf upper surface of mature leaves is green (RHS green 137A), leaf lower surface color of mature leaves is green (RHS green 137A), leaf upper surface of young leaves is green (RHS green 143A), and leaf lower surface color of young leaves is green (RHS green 144A). The stem bark color is greyed-green (RHS Grated-green 197A). The flower color of opened flower is white (RHS NN 155 White C), petal upper surface color is white (RHS NN 155 White C), and petal lower surface color is white (RHS NN 155 White C).

The tree growth habit is upright to spreading and the thorns are sparse. With regard to the shape of leaves, the shape of leaf is lanceolate, the apex of the leaf is acute, and the base of the leaf is aequilateral. Also, the leaf petiole has nectaries and is oval, the wavy edges of leaf blade are absent or weak and the incision of margin is crenate.

Also, as to the size of 'Jedae', the height of the tree is 154 cm to 184 cm, the tree spread is 178 cm to 232 cm, the tree vigor is strong, and the density of the tree is medium which is similar to 'Miyagawa-wase'.

As to the trunk of 'Jedae', the trunk diameter is 7.5 cm to 8.6 cm in diameter at a height of 15 cm above the ground for a 7-year-old tree, and the trunk texture is smooth which is similar to 'Miyagawa-wase'.

The winter hardness and cold/drought/heat tolerance of 'Jedae' are unknown.

2) Fruit Characteristics

Figure 8:
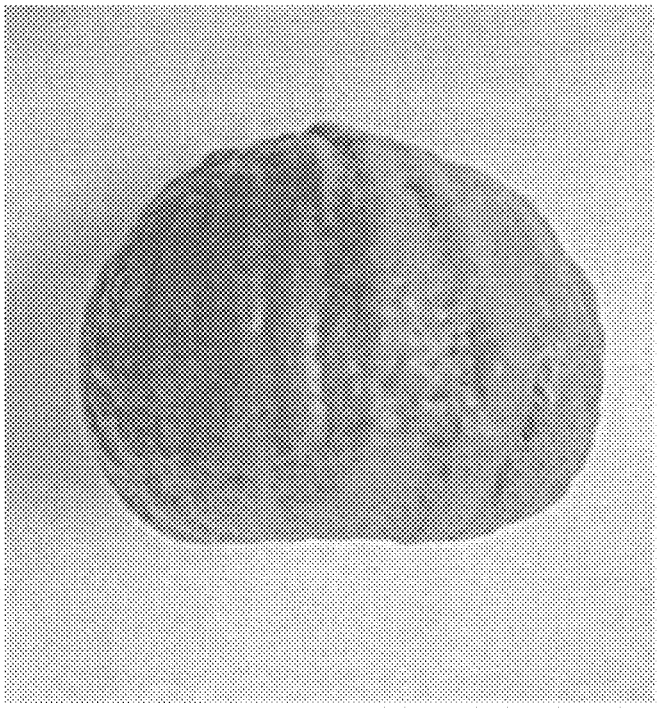
FIG. 8 shows a side view illustration of mature fruit of mutant *Citrus* 'Jedae' (the age of photographed 'Jedae': 7 years).
Figure 9:
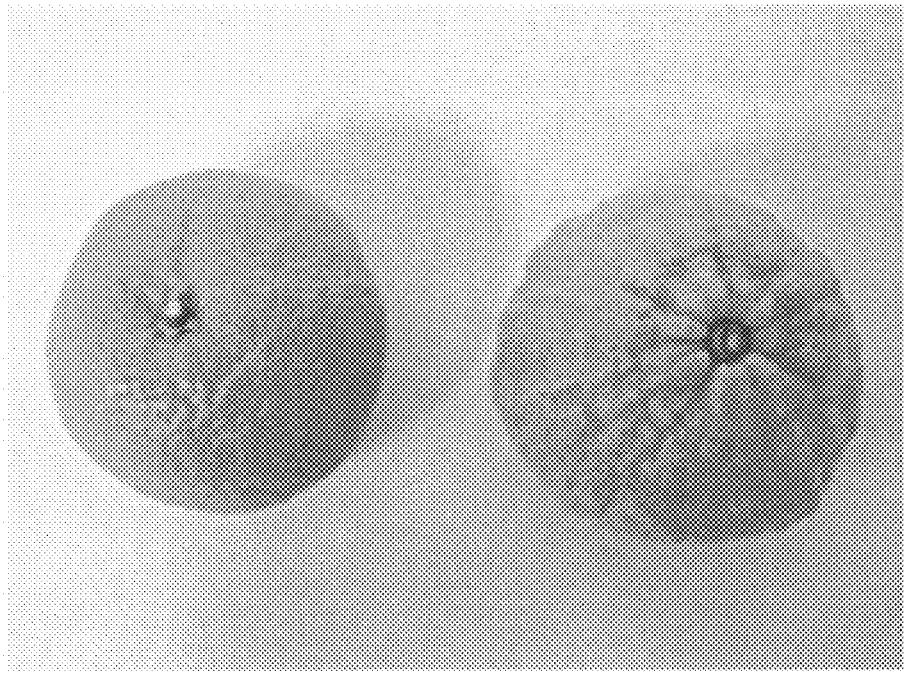
FIG. 9 shows the difference in external appearance of stalk (top) of *Citrus* between the fruit of mutant *Citrus* 'Jedae' (on the right side) and the fruit of 'Miyagawa-wase' (on the left side) (the age of photographed 'Jedae': 7 years).
Figure 10:
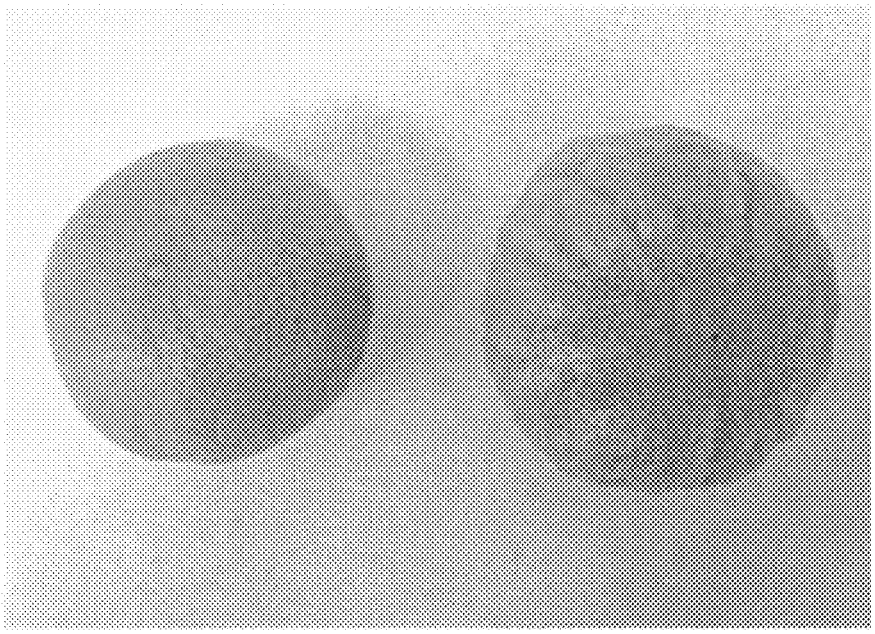
FIG. 10 shows the difference in external appearance of the rear (bottom) of *Citrus* between the fruit of mutant *Citrus* 'Jedae' (on the right side) and the fruit of 'Miyagawa-wase' (on the left side) (the age of photographed 'Jedae': 7 years).

FIG. 4 to FIG. 7 present the photographs of fruits of mutant *Citrus* named 'Jedae', which were taken in early July, early November, and early December, respectively, and the photographs of fruits of 'Miyagawa-wase', the mother plant, which were taken in early December. Moreover, FIG. 8 shows side view photograph of mature fruit of 'Jedae' and FIG. 9 shows the outer appearance of *Citrus* leaf stalk which is compared with that of 'Miyagawa-wase'. FIG. 10 shows the photograph that compares the outer appearance of rear part of the *Citrus* with that of 'Miyagawa-wase'.

The following shows fruit characteristics (Table 4).

TABLE 4

| Year | Longitudinal Diameter of Fruit (mm) | Transverse Diameter of Fruit (mm) | Fruit Weight (g) | Peel Thickness (mm) | Sugar Content (° Brix) |
|---|---|---|---|---|---|
| 2009 | 62.3 | 78.1 | 156.73 | 4.2 | 10.2 |
| 2010 | 54.8 | 66.5 | 131.6 | 2.1 | 7.8 |
| 2011 | 52.8 | 62.6 | 110.3 | 2.6 | 10.8 |
| 2013 | 34.9 | 46.3 | 41.1 | 2.5 | 11.8 |
| 2014 | 65.35 | 64.64 | 126.3 | 4.02 | 7.4 |

TABLE 4-continued

| Year | Acidity (wt %) | Hunter Color Value of Fruit: L (Light-ness) | a (Red-ness) | b (Yellow-ness) | Harvesting Period |
|---|---|---|---|---|---|
| 2009 | 0.97 | 64.41 | 33.95 | 64.66 | Mid December |
| 2010 | 0.78 | 67.78 | 29.56 | 72.44 | Early December |
| 2011 | 0.69 | 69.5 | 26.5 | 72.4 | Early December |
| 2013 | 0.85 | 66.48 | 30.69 | 68.77 | Early December |
| 2014 | 1.25 | 59.55 | 30.51 | 34.84 | Early December |

The fruits of 'Jedae' exhibited characteristics almost similar to the fruits of 'Miyagawa-wase' in terms of sugar content and acidity. The fruits of 'Jedae' were slightly larger than those of 'Miyagawa-wase'. In addition, the fruits of 'Jedae' had the peels that were less smooth and more rugged on outer surface in terms of fruit shape, compared to fruits of 'Miyagawa-wase'.

The fruits of 'Jedae' had groove of radial shape from the fruit stalk and were found to have vertical corrugation in overall way when they were viewed from the side. Thus, the fruits of 'Jedae' were considered to have excellent fruit shape and have the potential to be developed into decorative *Citrus* fruits.

In addition, the fruits generated from 'Jedae' maintain their altered shapes described above from young fruit bearing stage to maturation stage in early December, and can be harvested with those of 'Miyagawa-wase' almost around the same time. However, the fruits of 'Jedae' showed distinctive difference from those of 'Miyagawa-wase' in terms of fruit shape arising from changes in peel traits.

Figure 11:
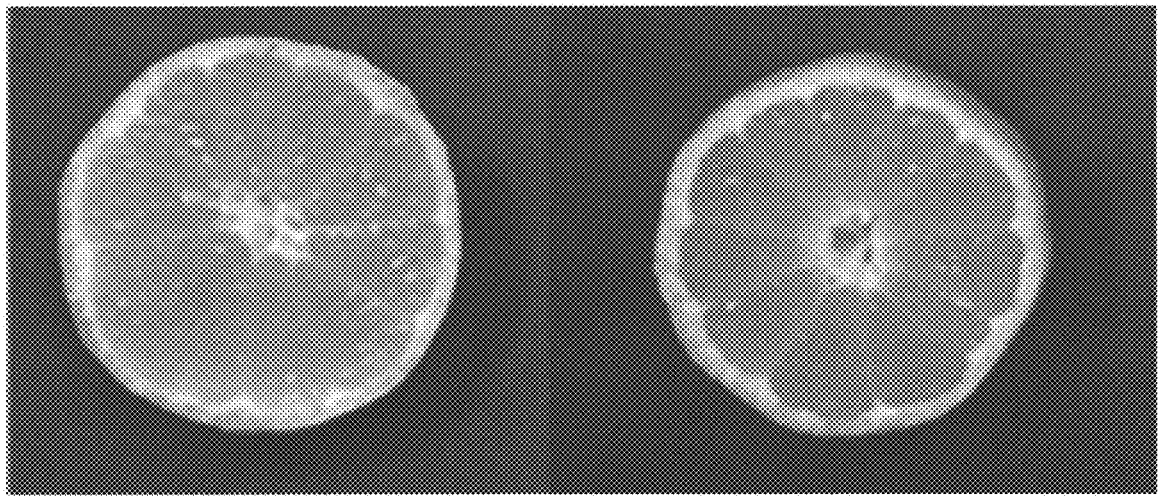
FIG. 11 shows the difference in *Citrus* fruit cross-section of between mutant *Citrus* 'Jedae' and 'Miyagawa-wase' (top and left side: 'Miyagawa-wase'/right side: 'Jedae') (the age of photographed 'Jedae': 7 years).
Figure 12:
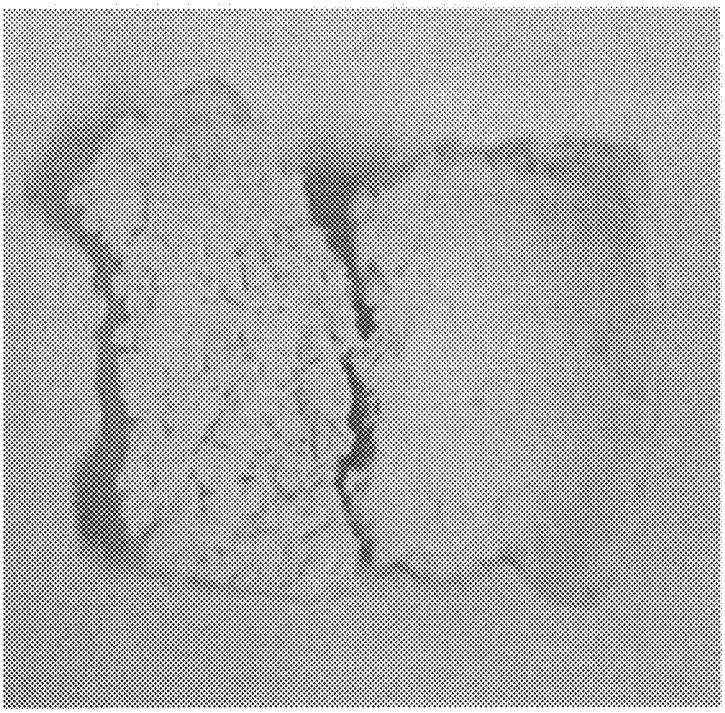
FIG. 12 shows the difference in white area (albedo layer) inside fruit peel between mutant *Citrus* named 'Jedae' and 'Miyagawa-wase' (bottom and left side: 'Miyagawa-wase'/right side: 'Jedae') (the age of photographed 'Jedae': 7 years).
Figure 13:
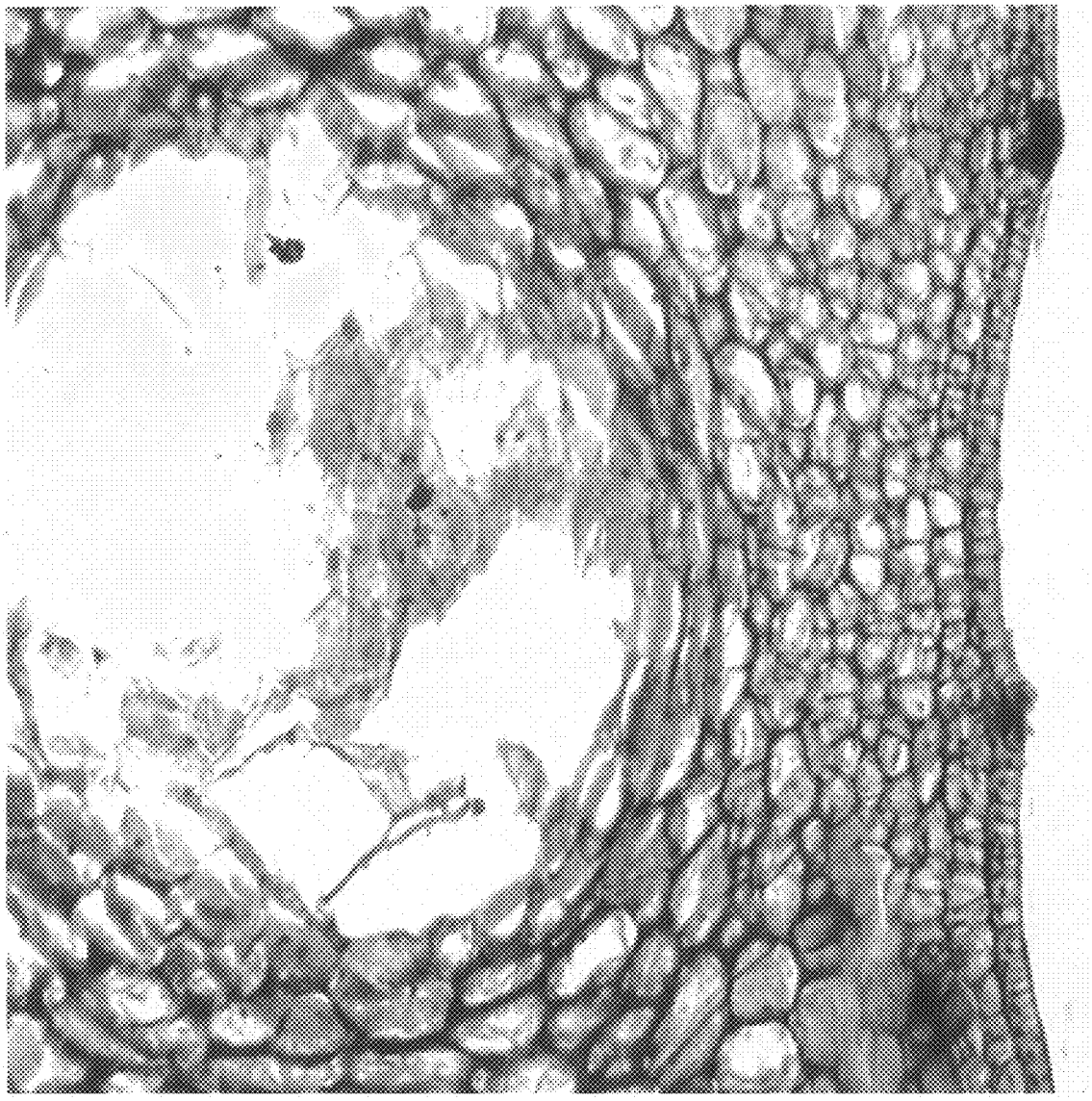
FIG. 13 shows the results of microscopic observation of the peel of young fruit (harvested in June 2013) of 'Miyagawa-wase' at cellular level (photographed 20×).
Figure 14:
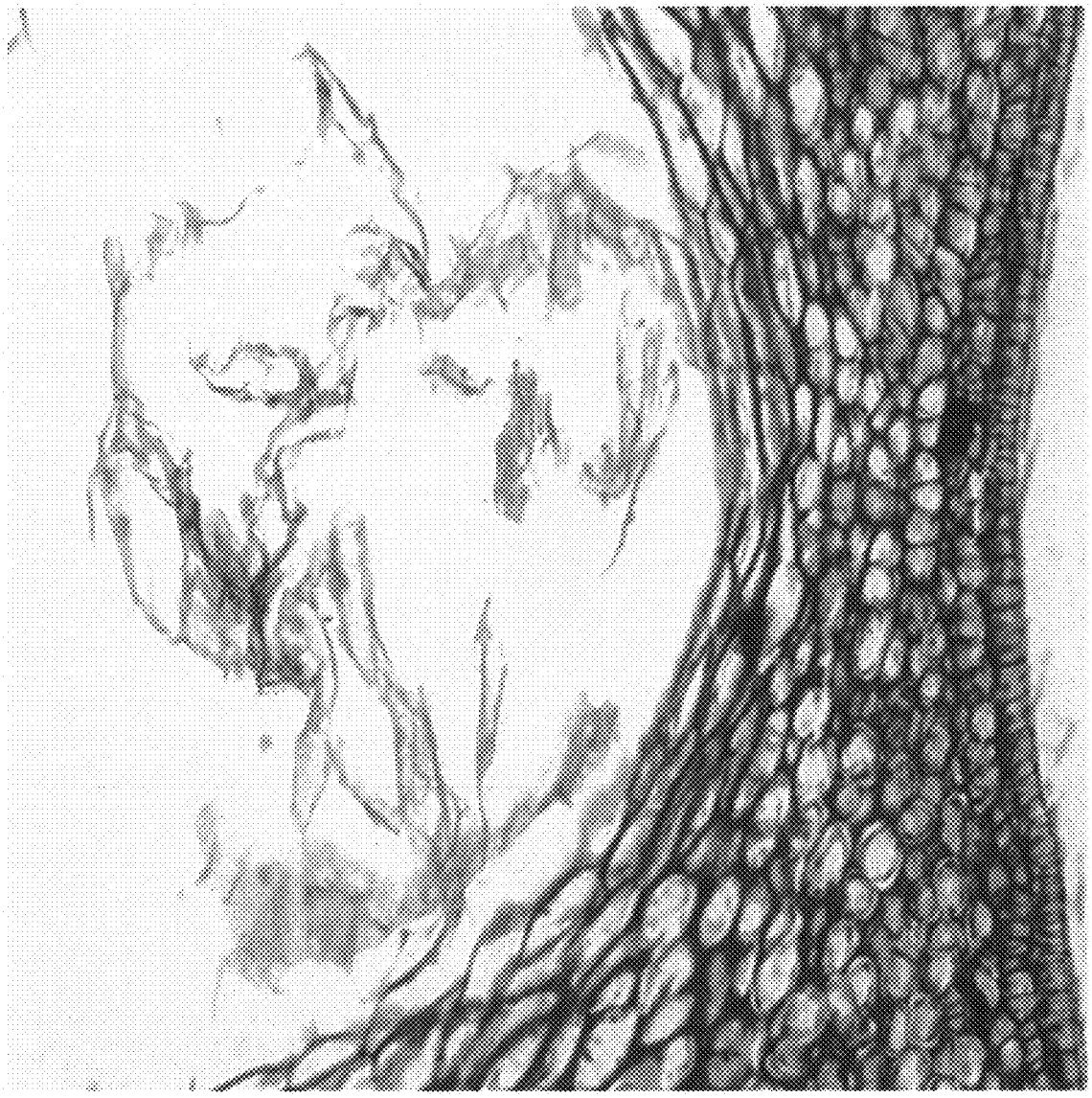
FIG. 14 shows the results of microscopic observation of the peel of young fruit (harvested in June 2013) of 'Jedae' at cellular level (photographed 20×).
Figure 15:
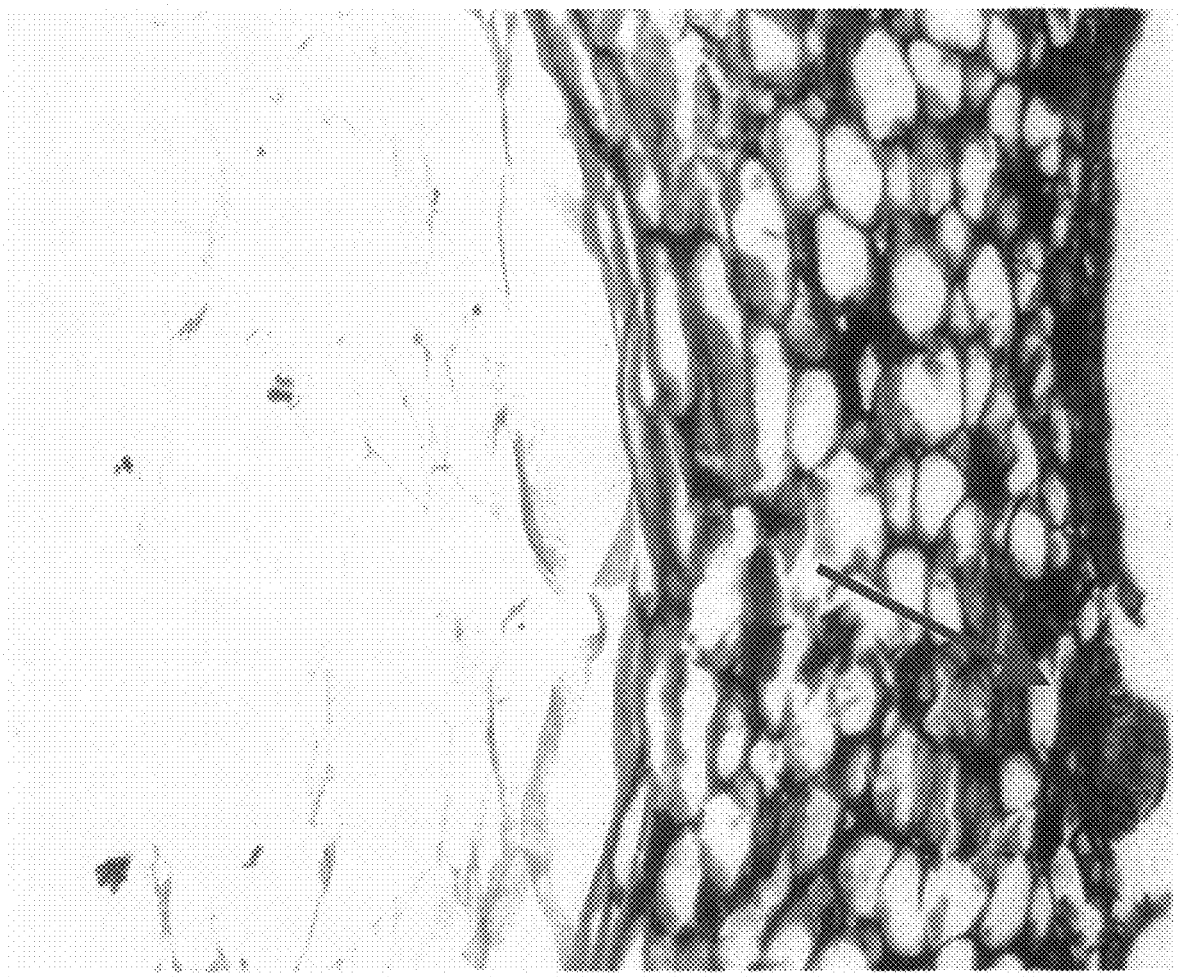
FIG. 15 shows the results of microscopic observation of the peel of mature fruit (harvested in December 2013) of 'Miyagawa-wase' at cellular level (photographed 40× and the arrow indicates the epidermal cell cytolysis).
Figure 16:
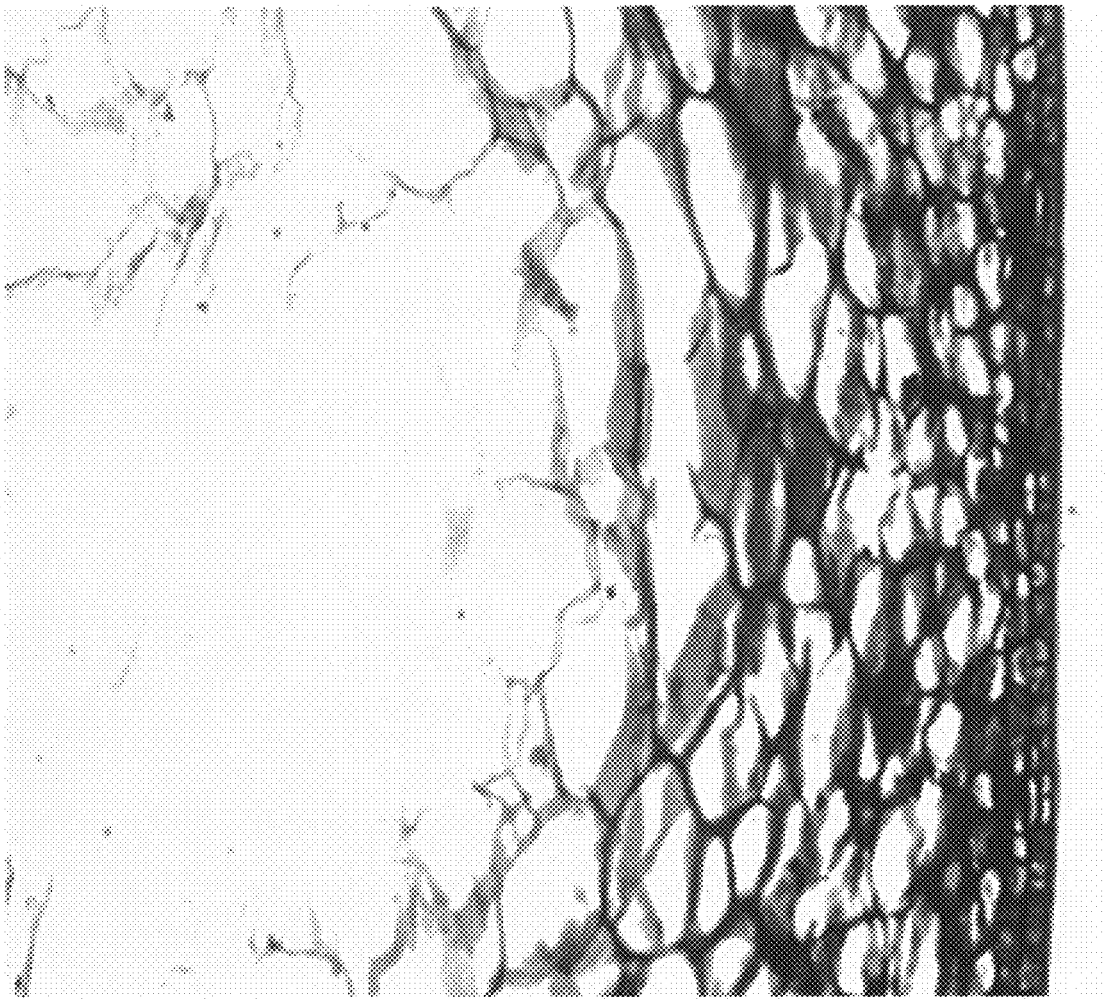
FIG. 16 shows the results of microscopic observation of the peel of mature fruit (harvested in December 2013) of 'Jedae' at cellular level (photographed 40×).
Figure 17:
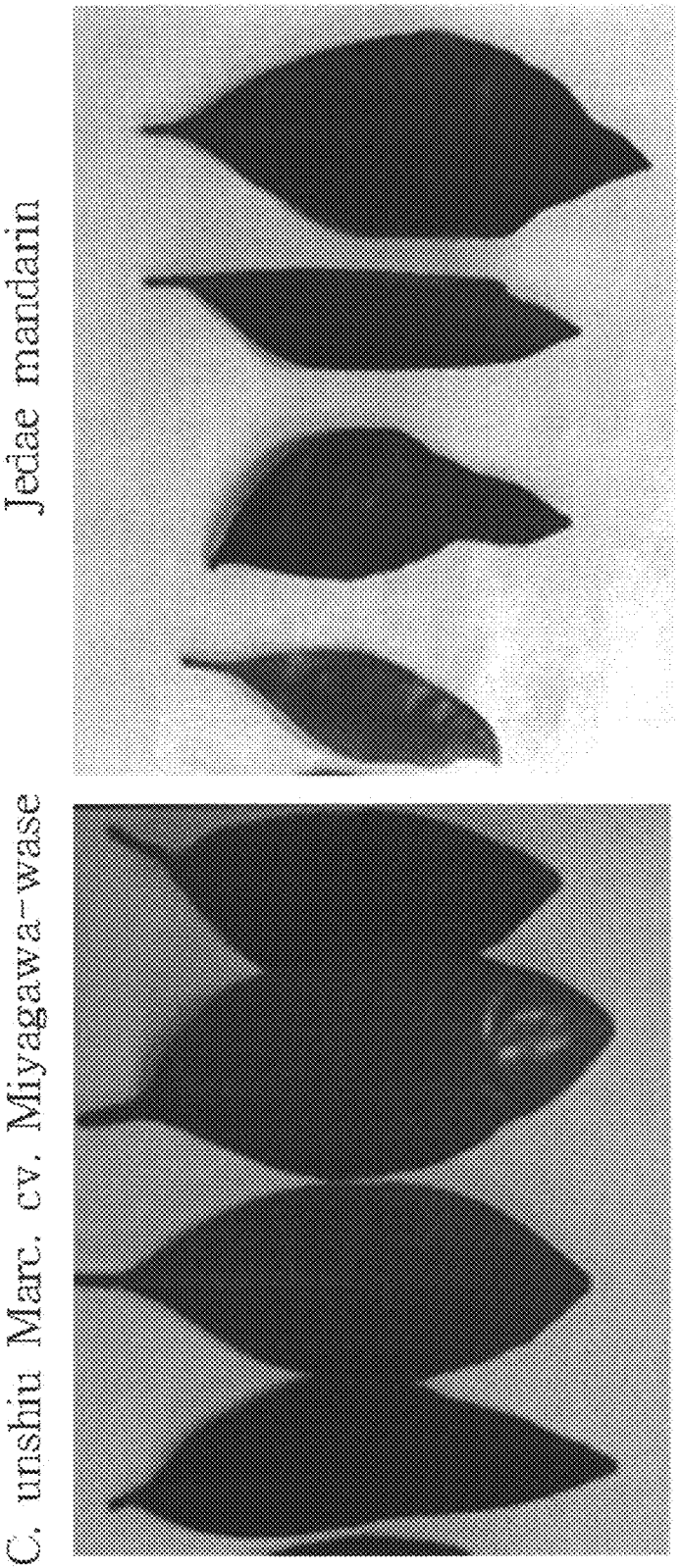
FIG. 17 shows leaf shapes between 'Jedae' *Citrus* tree and 'Miyagawa-wase' *Citrus* tree (the age of photographed 'Jedae': 7 years).

FIG. 11 shows the photograph that compares the *Citrus* section of 'Jedae' (right side) with the fruit section of 'Miyagawa-wase' (left side). FIG. 12 shows the photograph comparing the white portion (albedo layer) inside the peel ('Miyagawa-wase' (left side) and 'Jedae' (right side)).

FIG. 11 and FIG. 12 also show that 'Jedae' is characterized by smooth fiber not protruding roughly regarding the surface that comes into contact with fruit flesh in albedo layer, unlike 'Miyagawa-wase'. Therefore, the fruits of 'Jedae' showed good adhesion between fruit and fruit flesh and good storability, but could not be easily peeled.

As to the fruit color of 'Jedae', the fruit surface color is yellow orange (RHS orange 25A), fruit flesh color is light orange (RHS orange 26B), the fruit areola is absent, parthenocarpy is present, self-incompatibility is present, and seed is absent.

As to the productivity of the fruit of 'Jedae', the 7-year-old tree produces 11.4 kg to 26.5 kg per tree. The average weight per fruit is about 120 g.

What is claimed is:

1. A variant of *Citrus* plant of a novel variety named 'Jedae mandarin', substantially as illustrated and described herein.

* * * * *